US010717977B2

(12) United States Patent
LaBaer

(10) Patent No.: US 10,717,977 B2
(45) Date of Patent: *Jul. 21, 2020

(54) NUCLEIC ACID-TAGGED COMPOSITIONS AND METHODS FOR MULTIPLEXED PROTEIN-PROTEIN INTERACTION PROFILING

(71) Applicant: ARIZONA BOARD OF REGENTS ON BEHALF OF ARIZONA STATE UNIVERSITY, Scottsdale, AZ (US)

(72) Inventor: Joshua LaBaer, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/904,905

(22) Filed: Feb. 26, 2018

(65) Prior Publication Data

US 2018/0201923 A1  Jul. 19, 2018

Related U.S. Application Data

(63) Continuation of application No. 14/777,019, filed as application No. PCT/US2014/030226 on Mar. 17, 2014, now Pat. No. 9,938,523.

(60) Provisional application No. 61/792,666, filed on Mar. 15, 2013.

(51) Int. Cl.
*C12N 15/10*   (2006.01)
*G01N 33/68*   (2006.01)
*G01N 33/53*   (2006.01)

(52) U.S. Cl.
CPC ..... *C12N 15/1062* (2013.01); *G01N 33/6845* (2013.01); *G01N 33/6854* (2013.01); *G01N 2458/10* (2013.01)

(58) Field of Classification Search
None
See application file for complete search history.

(56) References Cited

U.S. PATENT DOCUMENTS

| 2005/0048580 | A1* | 3/2005 | Labaer | C07K 1/047 435/7.1 |
| 2013/0317207 | A1* | 11/2013 | Kirkland | C07D 471/06 536/26.8 |
| 2015/0299764 | A1* | 10/2015 | Raspe | C12Q 1/485 435/6.18 |

* cited by examiner

*Primary Examiner* — Changhwa J Cheu
(74) *Attorney, Agent, or Firm* — Quarles & Brady, LLP; Jessica L. Lewis

(57) ABSTRACT

Methods and compositions for multiplexed protein-protein interaction profiling (e.g., immunoprofiling), based on nucleic acid tagging of polypeptides (e.g., by RNA display) are described. In some embodiments the described compositions and methods utilize a library of prey polypeptide targets linked to prey RNAs encoding them, and a population of bait polypeptides, e.g., a mixture of antibodies, that bind to one or more of the prey polypeptide targets and are used to isolate and identify the bound prey polypeptide targets by amplification of their associated prey RNAs and sequencing of the corresponding cDNAs. In other embodiments the prey polypeptide targets are linked to DNA Bar Codes, which serve as unique identifiers of the tagged polypeptide.

20 Claims, 9 Drawing Sheets

Specification includes a Sequence Listing.

SEQUENCE LISTING

<160> NUMBER OF SEQ ID NOS: 2

<210> SEQ ID NO 1
<211> LENGTH: 297

```
<212> TYPE: PRT
<213> ORGANISM: Artificial Sequence
<220> FEATURE:
<223> OTHER INFORMATION: synthetic

<400> SEQUENCE: 1

Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
210                 215                 220

Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
            260                 265                 270

Leu Leu Gln Glu Asp Asn Pro Asp Leu Ile Gly Ser Glu Ile Ala Arg
        275                 280                 285

Trp Leu Ser Thr Leu Glu Ile Ser Gly
290                 295

<210> SEQ ID NO 2
<211> LENGTH: 34
<212> TYPE: DNA
<213> ORGANISM: Artificial Sequence
<220> FEATURE:
<223> OTHER INFORMATION: synthetic

<400> SEQUENCE: 2
aaaaaaaaaa aaataggccg ttgactcatc tacg                            34
```

NUCLEIC ACID-TAGGED COMPOSITIONS AND METHODS FOR MULTIPLEXED PROTEIN-PROTEIN INTERACTION PROFILING

CROSS-REFERENCE TO RELATED APPLICATIONS

This application is a continuation of U.S. patent application Ser. No. 14/777,019, filed Sep. 15, 2015, which represents the U.S. National Stage of International Application No. PCT/US2014/030226, filed Mar. 17, 2014, which claims the benefit of U.S. Provisional Patent Application Ser. No. 61/792,666 filed on Mar. 15, 2013, each of which is incorporated by reference herein as if set forth in its entirety.

BACKGROUND

Protein-protein interactions are a core theme running throughout biology in health and disease. For example, the immune system produces diverse high-affinity antibodies as an adaptive response to pathogens, and sometimes, as a maladaptive response to self-proteins in the context of autoimmune conditions. However, identifying the many interacting target proteins for multiple protein actors in parallel remains a daunting challenge. In particular, there is an ongoing need for methods and compositions that can apply ever-accelerating developments in "next generation," massively parallel DNA sequencing to the problem of identifying many protein-protein interaction targets in a multiplexed format, e.g., in medical diagnostics and personalized medicine applications.

BRIEF SUMMARY

Described herein are compositions and methods for the application of nucleic acid-tagged polypeptides to multiplexed identification of protein-protein interaction targets, e.g., a set of target antigens that is bound by a complex mixture of antibodies as is found in patient serum.

Accordingly, in a first aspect disclosed herein is a multiplexed polypeptide affinity assay (MPA) composition comprising a population of prey polypeptide targets (PPTs), wherein each PPT in the population is chemically linked to a prey nucleic acid, and wherein the relative abundance of PPTs in the population falls within about a ten fold range. In some embodiments the prey nucleic acid is an RNA encoding the amino acid sequence of the chemically linked PPT In some embodiments of the first aspect, the PPT population comprises a plurality of amino acid sequences from a plurality of pathogens (e.g., viral pathogens, bacterial pathogens, eukaryotic pathogens, or a combination thereof. In other embodiments, the PPT population comprises a plurality of amino acid sequences from a plurality of antigens associated with one or more autoimmune diseases. In further embodiments, the PPT population comprises a plurality of polypeptides comprising random amino acid sequences.

In some embodiments of the first aspect, the MPA composition also includes a population of bait polypeptides comprising diverse amino acid sequences, wherein at least one of the bait polypeptides binds to at least one of the prey nucleic acid-linked PPTs. In some embodiments, the population of bait polypeptides comprises at least three to about ten different polypeptides, wherein the polypeptides comprise at least a one amino acid difference in their amino acid sequences. In some embodiments, the population of bait polypeptides comprises a plurality of antibodies with diverse antigen specificities. In some embodiments, the population of bait polypeptides comprises serum (e.g., human serum).

In some embodiments of the first aspect, where the MPA composition includes a plurality of antibodies with diverse antigen specificities, the MPA composition also includes a polypeptide that binds specifically to the Fc region of an immunoglobulin. In some embodiments, the polypeptide that binds specifically to the Fc region of an immunoglobulin is Protein G, Protein A, Protein A/G, or an antibody that binds specifically to the Fc region of an immunoglobulin. In some embodiments, the plurality of antibodies in the MPA composition are biotinylated antibodies.

In some embodiments of the first aspect, where the MPA composition includes a population of bait polypeptides, the bait polypeptides comprise diverse amino acid sequences from at least one of transcription factors, G-proteins, receptors, protein kinases, protein phosphatases, proteases, or a combination thereof.

In other embodiments of the first aspect, where the prey nucleic acid is a prey RNA, the prey RNA comprises one or more modified ribonucleotides (e.g., RNAse-resistant ribonucleotides).

In some embodiments of the first aspect, the prey nucleic acid comprises a nucleotide sequence that does not occur naturally. In some embodiments, the nucleotide sequence that does not occur naturally is a bar code tag sequence In a second aspect disclosed herein is a kit, comprising: (i) a PPT library, wherein each PPT in the library is chemically linked to a synthetic prey nucleic acid (e.g., a prey RNA encoding the amino acid sequence of the chemically linked PPT; or a DNA bar code), and wherein the relative abundance of PPTs in the population falls within about a ten fold range; and (ii) forward and reverse oligonucleotide primers to reverse transcribe and amplify prey nucleic acids.

In some embodiments of the second aspect, the kit comprises a PPT library comprising a population of prey RNA sequences that do not occur together naturally in the same tissue or cell type.

In other embodiments of the second aspect, the PPT library comprises a plurality of amino acid sequences from a plurality of pathogens. In some embodiments, the plurality of amino acid sequences comprises amino acid sequences of viral pathogens, bacterial pathogens, eukaryotic pathogens, or a combination thereof.

In some embodiments of the second aspect, the PPT library comprises a plurality of amino acid sequences from a plurality of antigens associated with autoimmune diseases.

In some embodiments of the second aspect, where the prey nucleic acid is a prey RNA, the prey RNA comprises modified ribonucleotides (e.g., ribonuclease-resistant modified ribonucleotides).

In some embodiments of the second aspect, the kit also includes a polypeptide selected from the group consisting of Protein A, Protein G, and Protein A/G.

In some embodiments of the second aspect, the kit also includes oligonucleotide primers for reverse transcription and amplification of the prey RNA. In some embodiments, one or more of the included oligonucleotide primers comprises a bar code tag sequence.

In a third aspect disclosed herein is method for antigen immunoprofiling a biological sample, comprising:
(i) providing a biological sample, to be immunoprofiled, comprising a plurality of antibodies with diverse antigen specificities;
(ii) contacting the biological sample with a population of PPTs, wherein each PPT in the population is chemically linked to a prey nucleic acid, and wherein the contacting conditions permit binding of one or more of the antibodies in the plurality of antibodies in the biological sample to one or more of the PPTs in the population of PPTs to obtain one or more antibody-PPT complexes;

(iii) immunoprecipitating the one or more antibody-PPT complexes;

(iv) amplifying prey nucleic acid sequences associated with the one or more immunoprecipitated antibody-PPT complexes to obtain a plurality of cDNAs comprising nucleic acid sequences corresponding to the amplified prey RNA sequences; and (v) sequencing the plurality of cDNAs to obtain an antigen immunoprofile of the biological sample.

In some embodiments the prey nucleic acid is a prey RNA encoding the amino acid sequence of the chemically linked PPT In some embodiments of the third aspect, the biological sample to be evaluated comprises serum.

In some embodiments of the third aspect, the prey nucleic acid used in the method comprises a nucleotide sequence that does not occur naturally. In some embodiments of the method, the prey comprises one or more modified ribonucleotides. In some embodiments the prey nucleic acid is a DNA bar code.

In some embodiments of the third aspect, the population of PPTs comprises one or more PPTs the amino acid sequences of which are from a pathogen. In some embodiments, where the population of PPT comprises one or more pathogen amino acid sequences, the biological sample to be tested comprises serum from a subject exposed to a pathogen or suspected of being exposed to the pathogen.

In some embodiments of the third aspect, the population of PPTs used in the method comprises one or more cancer cell PPTs.

In some embodiments of the third aspect, the biological sample used in the method comprises antibodies from multiple subjects suffering from the same health condition or diagnosed as being at risk for the same health condition.

In some embodiments of the third aspect, amplifying the prey RNA sequences also includes incorporating a bar code tag sequence into the plurality of cDNAs resulting from the amplification.

In a fourth aspect disclosed herein is a method for identifying a disease-associated antigen, comprising: (i) providing a first biological sample, comprising a plurality of antibodies from one or more control subjects; (ii) contacting the first biological sample with a population of PPTs, wherein each PPT in the population of PPTs is chemically linked to a prey nucleic acid, and wherein the contacting conditions permit binding of one or more of the PPTs with one or more of the antibodies in the plurality of antibodies from the one or more control subjects to obtain one or more control subject antibody-PPT complexes; (iii) immunoprecipitating the one or more control antibody-PPT complexes to obtain a counter-selected PPT population comprising a population of PPTs depleted of PPTs recognized by antibodies present in the first biological sample; (iv) contacting the counter-selected PPT population with a second biological sample comprising a plurality of antibodies from one or more patients suffering from the same health condition or diagnosed as being at risk of suffering from the same health condition to obtain one or more patient antibody-PPT complexes; (v) immunoprecipitating the one or more patient antibody-PPT complexes; (vi) amplifying prey nucleic acid sequences associated with the one or more immunoprecipitated patient antibody-PPT complexes to obtain a plurality of disease antigen-associated cDNAs comprising nucleic acid sequences corresponding to the amplified prey nucleic acid sequences; and (vii) sequencing the plurality of cDNAs to identify the disease-associated antigen.

In some embodiments the prey nucleic acid is a prey RNA encoding the amino acid sequence of the chemically linked PPT In some embodiments of the fourth aspect, the health condition is an infectious disease. In some embodiments, where the health condition is an infectious disease, the population of PPTs comprises pathogen PPTs.

In some embodiments of the fourth aspect, the prey RNA comprises a nucleotide sequence that does not occur naturally.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

DETAILED DESCRIPTION

Figure 1:
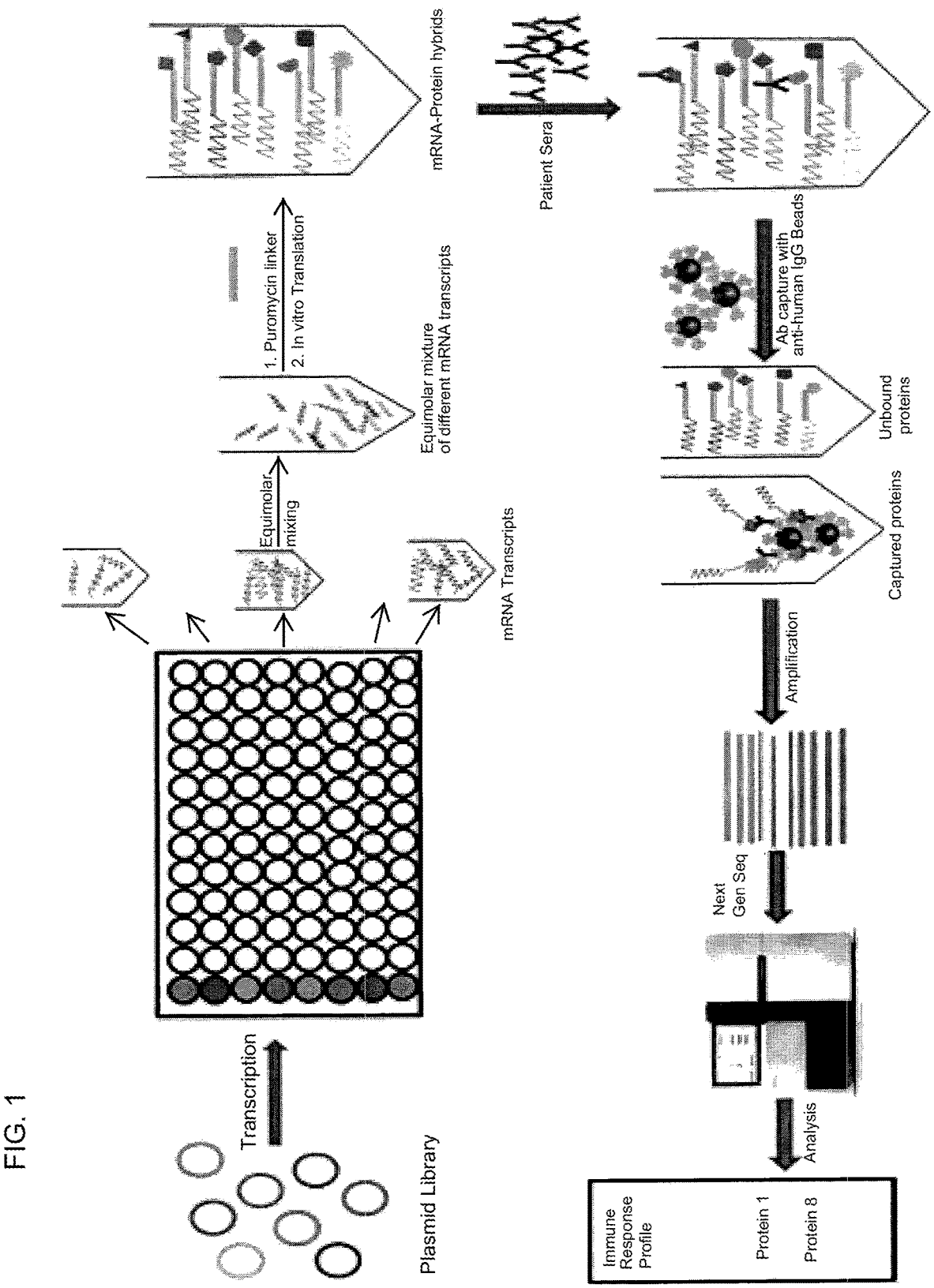
FIG. 1 shows a schematic illustration of a non-limiting embodiment of the described methods. A library of individual plasmids, each encoding a unique gene, is delivered to the wells of a 96-well plate. Each is transcribed, and the resulting RNAs are mixed in equimolar amounts. The mixed RNAs are used to create an mRNA display mix of protein-RNA hybrids, which are then probed with the serum of patients or controls. Proteins bound to serum are separated from the mix and the attached RNAs are copied into DNA and amplified. The resulting DNA is sequenced yielding information about immune response profile of the patient or control.
Figure 2:
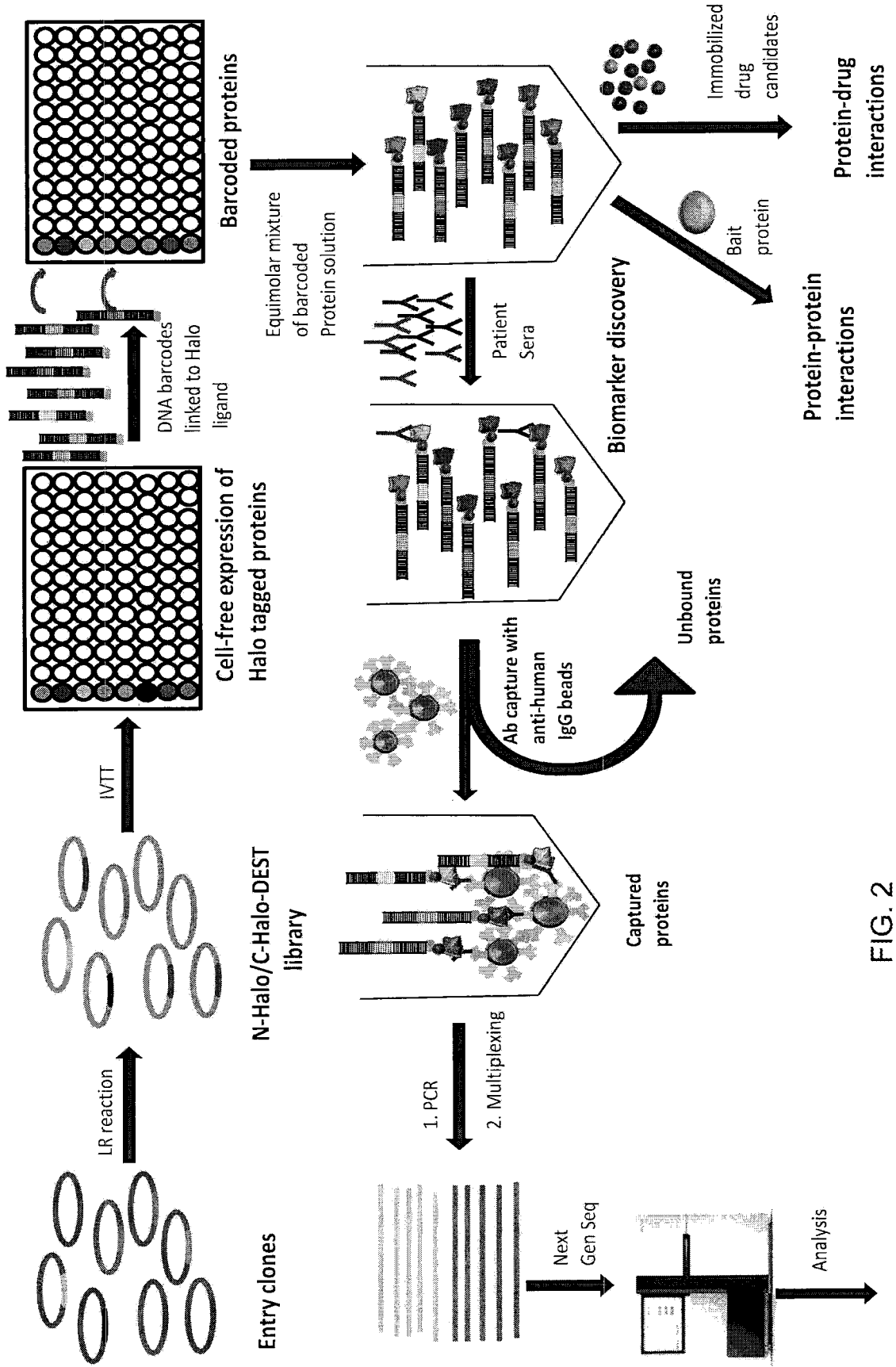
FIG. 2 Identifying biomarkers using nucleic acid tagged proteins. Genes encoding various proteins are transferred into a plasmid vector that appends a polypeptide capable of forming a covalent attachment to a nucleic acid or chemical attached to a nucleic acid. The protein is produced and subsequently linked to a nucleic acid with a unique sequence, adding an effective bar code. A mixture of similarly labeled proteins is subjected to a selection by patient serum, and the patient's antibodies that bind certain proteins are separated, from unbound antibodies. To determine which proteins were recognized by patient serum, the nucleic acids attached to the captured proteins are amplified and subjected to DNA sequencing.

Disclosed herein are compositions and methods for multiplexed identification of polypeptides based on the combined use of nucleic acid tagging of such "prey polypeptide targets" and their binding interactions with "bait" polypeptides within a mixture of diverse bait polypeptides, e.g., a mixture of antibodies or other polypepetides of diverse binding specificities.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

Definitions

In describing the embodiments and claiming the invention, the following terminology will be used in accordance with the definitions set out below.

As used herein, "about" means within 5% of a stated range within the relevant parameter.

As used herein, "bait polypeptide," refers to a polypeptide that has specific affinity for at least one "prey polypeptide target."

As used herein, "prey polypeptide target," refers to a polypeptide for which one or more bait polypeptides (e.g., an antibody) have specific affinity. The amino acid sequence of a prey polypeptide target can range from at least 5 amino acids to about 2000 amino acids.

As used herein, "population of PPTs" or "PPT library" refer to a heterogeneous mixture of polypeptides containing diverse amino acid sequences.

With respect to the amino acid sequence homology of polypeptides described herein, one of ordinary skill in the art will appreciate that structural and functional homology of two or polypeptides generally includes determining the percent identity of their amino acid sequences to each other. Sequence identity between two or more amino acid sequences is determined by conventional methods. See, for example, Altschul et al., (1997), Nucleic Acids Research, 25(17):3389-3402; and Henikoff and Henikoff (1982), Proc. Natl. Acad. Sci. USA, 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as: ([Total number of identical matches]/[length of the longer sequence plus the number of gaps introduced into the longer sequence in order to align the two sequences])(100).

Compositions

Described herein are multiplexed polypeptide affinity (MPA) assay compositions, which include at least a population of prey polypeptide targets (PPTs), where each PPT in the population is chemically linked, e.g., through a puromycin linker, to a prey nucleic acid (e.g., an RNA encoding the amino acid sequence of the chemically linked PPT, or a DNA "bar code"), and where the relative abundance of the PPTs in the population falls within about a ten fold range.

In some embodiments, prey nucleic acids used in the compositions and methods described herein are prey RNAs typically generated by in vitro transcription of cDNAs encoding polypeptides of interest followed by ligation by RNA T4 ligase to a puromycin-adaptor-linker, as described in, e.g., WO2005/024018 entitled "Nucleic Acid Construct and process for producing the same," and Shibui et al (2008), *Biotechnol Lett* 30:2037-2043. Prey RNAs are then translated in vitro to obtain prey polypeptide targets that are covalently attached to their RNA transcripts via puromycin, a peptidyl acceptor antibiotic. The covalent linkage is generated by the translation in vitro of synthetic RNAs that carry puromycin at their 3'-end. During the translation process, ribosomes reach the junction between the RNA transcript and the chemically synthesized linker and stall, which allows the puromycin on the other side of the spacer to enter the ribosomal A-site and form a stable amide bond with the encoded polypeptide (See Nemoto et al (1997), *FEBS Lett,* 414(2):405-408). In vitro systems for transcription and translation are well known in the art and are commercially available, e.g., from Ambion and Life Technologies.

The use of "normalized" prey RNA populations to limit differences in the relative abundance of PPTs within a PPT population is an important advantage of the compositions and methods presented herein with respect to the use of RNA display, as practiced to date, using mRNA or cDNA samples (e.g., cDNA libraries) that are not normalized. The representation of a given sequence in such conventional cDNA samples and libraries is severely biased by its abundance in a starting mRNA sample (e.g., from a particular tissue), which could be as little as 1 copy/cell. Accordingly, a PPT antigen generated from a rare cDNA in a population of other cDNAs would be in very low abundance in a PPT population and might not be detectable.

In some embodiments, the relative abundance of PPTs in a PPT population falls within a range of about 2 fold to about 20 fold, e.g., about 3 fold, 4 fold, 5 fold, 7 fold, 10 fold, 12 fold, 15 fold, or another relative abundance range from about 2 fold to about 20 fold.

In some embodiments, the cDNAs are provided as plasmid templates comprising an RNA polymerase promoter sequence (e.g., SP6 or T7 RNA polymerase promoters) operably linked to the sequence to be transcribed. In preferred embodiments, the plasmids are provided from a normalized cDNA library in which representation of clone sequences is approximately equal or at least falls within a ten fold range of representation, i.e., the largest difference in sequence representation in the library is no greater than ten fold. In some the cDNA libraries may be arrayed libraries or clone collections (e.g., ORF collections) in which clones are maintained separately. In the case of arrayed libraries or clone collections, in some embodiments prey RNA transcription and translation reactions to generate PPTs are carried out using individual, or small subsets of clones in separate reactions followed by mixing of the resulting PPTs. In other embodiments, clones (e.g., plasmids) are mixed together in roughly equal proportions and prey RNA transcription and translation is performed in a combined reaction to obtain the PPT population used in the MPA compositions described herein. In further embodiments, clones are initially mixed together based on cDNA insert size range. By avoiding initial mixing of short insert clones with larger insert clones, the efficiency of large insert transcription is enhanced, as transcription of long inserts does not compete with the inherently more efficient transcription of shorter insert templates. In other embodiments, normalized libraries may be provided as pre-made mixtures of clones in which sequence representation falls within a limited range of relative abundance, as described herein.

In some embodiments, where the prey nucleic acids are prey RNAs, the prey RNA transcripts used in the MPA compositions contain modified ribonucleotides compatible with enzymatic synthesis of RNA transcripts, e.g., ribonuclease-resistant ribonucleotides, biotinylated ribonucleotides, or fluorescently labeled ribonucleotides.

Prey RNA populations used to generate PPT populations in MPA compositions can comprise nucleotide sequences from various sources, e.g, naturally occurring sources such as sequences found in tissue or cell culture-isolated mRNA samples or cDNA libraries. In some embodiments, the PPT population is generated from an open reading frame (ORF) collection (e.g, an arrayed library of clones encoding PPT sequences). Examples of such ORF collections include, but are not limited to, human proteome plasmid collections such as those available through DNASU (accessible through the website dnasu.asu.edu/DNASU/CollectionOverview.jsp), the human ORFeome collection at the Dana Farber Cancer Institute (accessible through the website horfdb.dfci.harvard.edu/hv7/).

Figure 3:
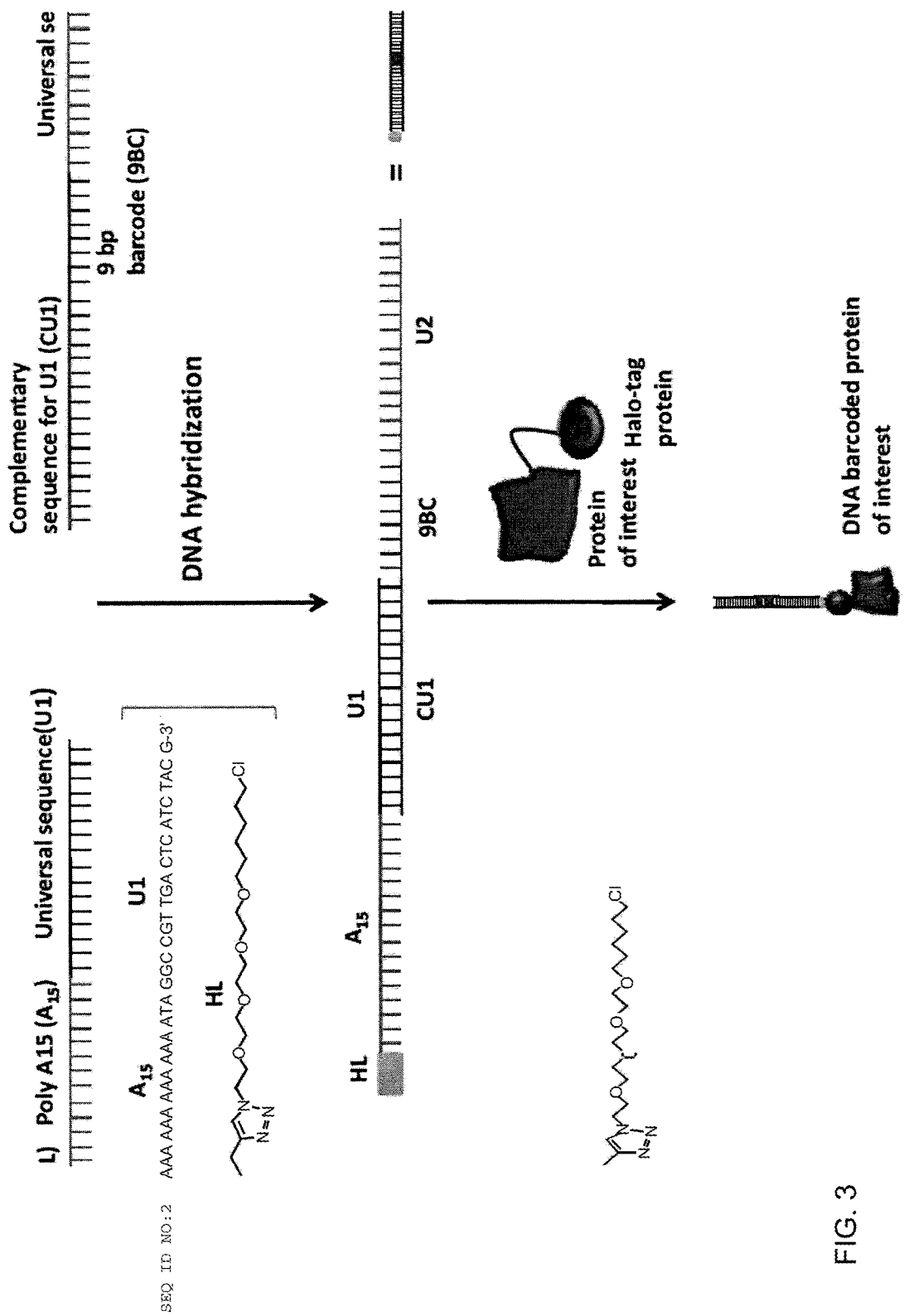
FIG. 3 Schematic overview of tagging four human proteins with nucleic acid bar codes. DNA bar code containing a polyA sequence; a "universal" sequence (U1); and a unique bar code is conjugated with a HaloTag® ligand (HL), which reacts specifically with a HaloTag®-fusion polypeptide.

In some embodiments prey nucleic acids are DNA bar codes comprising an a specific nucleic acid sequence that can be amplified, and which serves provides a unique identifier sequence associated with the prey polypeptide to which it is linked. In some embodiments, the DNA bar code is about 10 to 70 bases in length, e.g., about 12, 14, 18, 20, 22, 25, 30, 32, 35, 40, 45, 50, 60, 65, or another number of bases in length from about 10 to about 70 bases. In some embodiments, the nucleic acid sequence comprises a unique restriction site, which serves as a convenient identifying feature associated with a linked PPT, which can be identified by a simple restriction digest following amplification of the DNA bar code. In some embodiments, the DNA bar code, comprises a 5' polydA sequence (e.g., about 12-20 dAs) followed by a first universal sequence (e.g., about 12-30 bases in length); followed by a unique bar code sequence (e.g., about 9-12 bases, which serves an identifier for the specific tagged polypeptide); followed by a second universal sequence (e.g., about 12-30 bases in length) on the 3' end. One embodiment of this DNA bar coding configuration is illustrated in FIG. 3.

In some embodiments, PPTs are fusion polypeptides, which comprise the amino acid sequence of a haloalkane dehalogenase tag ("HaloTag®"; SEQ ID NO1:) polypeptide fused at their N-terminus or C-terminus.

```
(HaloTag ® Amino Acid Sequence)
                                          SEQ ID NO: 1
MAEIGTGFPFDPHYVEVLGERMHYVDVGPRDGTPVLFLHGNPTSSYVWRN

IIPHVAPTHRCIAPDLIGMGKSDKPDLGYFFDDHVRFMDAFIEALGLEEV

VLVIHDWGSALGFHWAKRNPERVKGIAFMEFIRPIPTWDEWPEFARETFQ

AFRTTDVGRKLIIDQNVFIEGTLPMGVVRPLTEVEMDHYREPFLNPVDRE

PLWRFPNELPIAGEPANIVALVEEYMDWLHQSPVPKLLFWGTPGVLIPPA

EAARLAKSLPNCKAVDIGPGLNLLQEDNPDLIGSEIARWLSTLEISG
```

Where the PPTs are fusion polypeptides comprising a HaloTag® amino acid sequence, DNA bar codes comprise a HaloTag® ligand comprising the structure of Formula I shown below, which enables efficient and convenient chemical linkage of the DNA bar code to the PPT via its reaction with the fused HaloTag® amino acid sequence:

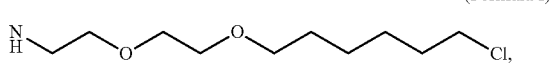
(Formula I)

DNA-conjugated HaloTag® ligands can be generated by conjugating a DNA bar code sequence with a HaloTag® ligand "building" block comprising a suitable reactive group, which reacts with the DNA to form a covalent linkage. Suitable examples of such HaloTag® ligand building blocks include:

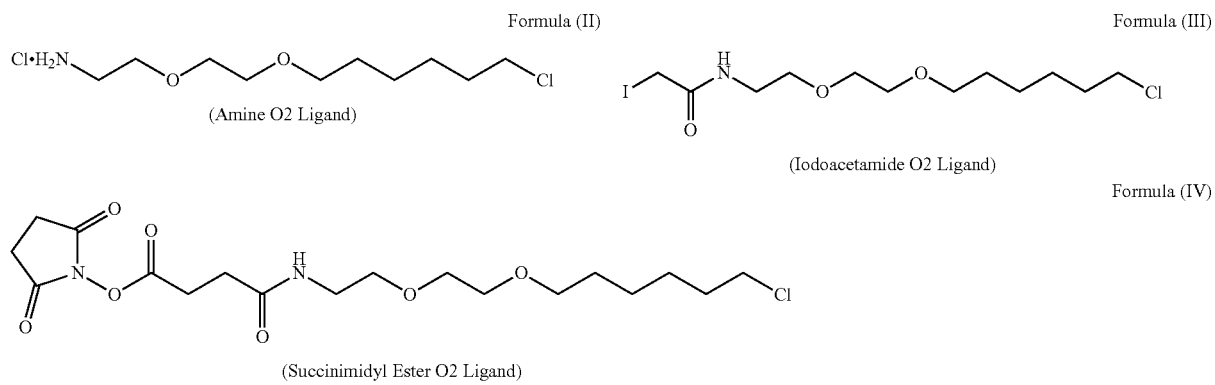

HaloTag® polypeptide expression vectors and building block ligands are available commercially from Promega (Madison, Wis.) and are conjugated with nucleic acids according to the manufacturer's instructions. In some embodiments, to conjugate a HaloTag® ligand to a DNA sequence, the DNA sequence is modified with an alkyne group (Integrated DNA technology). The azido halo ligand is then reacted with the alkyne terminated DNA sequence using the Cu-catalyzed cycloaddition ("click" chemistry). See, e.g., Duckworth et al (2007), *Angew Chem. Int.,* 46, Issue 46, pages 8819-8822

Alternatively, other fusion peptide tag-ligand capture moiety systems can be used, e.g., O6-alkylguanine-DNA alkyltransferase, reacts specifically and rapidly with benzylguanine (BG) (known as the SNAP-tag® system from New England Biolabs) or the "CLIP-tag®" variant of this system, also from New England Biolabs). See also Keppler et al (2003), *Nat Biotechnol,* (1):86-99; and Gautier et al (2008), *Chem. Biol,* 15(2):128-136.

In some embodiments, the PPT population comprises a plurality of polypeptides comprising a plurality of amino acid sequences derived from pathogens including, but not limited to, viral pathogens, bacterial pathogens, parasitic pathogens, or a combination thereof. In other embodiments, the PPT population comprises a plurality of amino acid sequences from a plurality of antigens associated with one or more autoimmune diseases. Examples of such autoimmune diseases include, but are not limited to, multiple sclerosis, Addison's disease, autoimmune hepatitis, Berger's disease, Celiac disease, chronic inflammatory demyelinating polyneuropathy, ulcerative colitis, Crohn's disease, psoriasis, rheumatoid arthritis, atopic dermatitis, Celiac disease, eczema, fibrodysplasia, Grave's disease, scleroderma, vitiligo, Diabetes mellitus type 1, Lupus erythematosus, and Meniere's disease. may comprise selected collections of nucleotide sequences that do not normally occur together naturally. In some embodiments, the PPT population comprises random sequence polypeptides. While not wishing to be bound by theory, such random sequence polypeptide populations are useful for generating an immunoprofile associated with a health condition. For example, autoantibodies associated with both Alzheimer's Disease and Parkinson's Disease have been detected by the use of random peptide libraries as antigens (Nagele et al (2011), *PLoS One.* 6(8):e23112; and Han et al (2012), *PLoS One,* 7(2):e32383).

In a number of embodiments, the MPA compositions presented herein contain, in addition to a PPT population, a population of bait polypeptides comprising diverse amino acid sequences, where at least one of the bait polypeptides binds to at least one of the nucleic acid-linked PPTs. In some embodiments, the bait polypeptide population comprises antibodies with diverse antigen specificities including one or more antigen specificities for a PPT in the PPT population provided in the MPA composition. For example, in some embodiments, the bait polypeptide population comprising antibodies may be provided in the form of a serum sample (e.g., a human serum sample) or a whole blood or serum fraction that contains a complex mixture of antibodies.

In some embodiments, where the bait polypeptide population comprises antibodies, the provided antibodies are biotinylated, which allows "pull-down" assays of antibody-prey polypeptide target complexes using avidin/streptavidin.

In other embodiments, where the bait polypeptide population comprises antibodies, the MPA composition also includes a polypeptide that binds specifically to the Fc region of an immunoglobulin, e.g., Protein G, Protein A, Protein A/G, or an antibody that binds specifically to the Fc region of an immunoglobulin, all of which are useful in pull-down assays of antibody-prey polypeptide target complexes.

In other embodiments, the bait polypeptide population comprises diverse amino acid sequences, e.g., amino acid sequences found in at least one of transcription factors, G-proteins, receptors, protein kinases, protein phosphatases, proteases, or a combination of sequences from these categories. In some cases, the number of different bait polypeptide amino acid sequences is about two to about 10, which is particularly useful when the identity of both a PPT and an interacting bait polypeptide need to be determined. In other embodiments, the number of bait polypeptide sequences is about 20 to about 100. In further embodiments, the number of bait polypeptides is about 100 to about 1,000.

Also provided herein are kits that include: (i) PPT library, wherein each PPT in the library is chemically linked to a prey nucleic acid (e.g., a synthetic prey RNA encoding the amino acid sequence of the chemically linked PPT, or a DNA bar code), and wherein the relative abundance of PPTs in the population falls within about a ten fold range; and (ii) forward and reverse oligonucleotide primers to reverse transcribe or amplify the prey nucleic acid.

In some embodiments, the PPT library in such kits will contain a population of prey nucleic acid sequences representing RNA sequences that do not occur together naturally in the same tissue or cell type. For example, where the prey nucleic acid sequences are prey RNA sequences, the population of prey RNA sequences may contain sequences encoding the entire human proteome, which are encoded by RNAs that clearly are expressed in different tissues, e.g., brain, liver, skin, kidney, heart etc or may contain cell type or subtype specific sequences including, but not limited to, sequences specific to T-cells, B-cells, natural killer cells, hepatocytes, cardiomyocytes, neurons, astrocytes, keratinocytes, lung epithelial cells, and myocytes.

Alternatively, the PPT library comprises diverse amino acid sequences from multiple pathogens, e.g., including, but not limited to, viral pathogens, bacterial pathogens, parasitic pathogens, or a combination thereof. In other embodiments, the PPT population comprises a plurality of amino acid sequences from a plurality of antigens associated with one or more autoimmune diseases. Examples of such autoimmune diseases include, but are not limited to, multiple sclerosis, Addison's disease, autoimmune hepatitis, Berger's disease, Celiac disease, chronic inflammatory demyelinating polyneuropathy, Diabetes mellitus type 1, Lupus erythematosus, and Ménière's disease.

In some embodiments, where the prey nucleic acid sequences are prey RNAs, the PPT-linked synthetic prey RNA included in the kit includes modified ribonucleotides, e.g., ribonuclease resistant ribonucleotides.

Optionally, the kits disclosed herein can also include, separately from the PPT library, Protein A, Protein G, or Protein A/G, any of which bind to the Fc portion of antibodies and are useful for precipitating antibodies or antibody-PPT complexes, which allows downstream identification of the immunoprecipitated PPT by the methods described herein.

In some embodiments, the forward or reverse oligonucleotide primers used to reverse transcribe or amplify prey nucleic acids, contain a bar code tag sequence. For example, where the prey nucleic acids are prey RNAs, the kit may provide a set of separate primers that are used for reverse transcription of prey RNA, have identical 3' sequences, but distinctive bar code sequences on the 5' end. Thus, by using reverse transcription primers with distinct bar code sequences in separate PPT library-sample reactions, the amplicons obtained from each sample can later be pooled for sequencing and distinguished from each other on the basis of the associated barcode tag sequences that were used in the separate reverse transcription reactions.

Methods

In many health conditions, it is desirable to determine an associated patient immune response. In some cases, the goal is to identify a specific antigen out of many possible antigens, which is triggering a patient immune response and is associated with a health condition, e.g., a pathogen-associated antigen such as a viral coat protein, or an autoimmune-associated antigen such as myelin basic protein. In other instances, the objective is to determine a global response of a patient's immune system, by detecting and quantifying, in a patient sample comprising antibodies, antibody reactivity with a provided population of antigens, i.e., a method for "immunoprofiling" a biological sample.

As described herein, a method for immunoprofiling a biological sample includes the steps of: (i) providing a biological sample, to be immunoprofiled, comprising a plurality of antibodies with diverse antigen specificities; (ii) contacting the biological sample with a population of PPTs, wherein each PPT in the population is chemically linked to a prey nucleic acid encoding the amino acid sequence of the chemically linked PPT, and wherein the contacting conditions permit binding of one or more of the antibodies in the plurality of antibodies in the biological sample to one or more of the PPTs in the population of PPTs to obtain one or more antibody-PPT complexes; (iii) immunoprecipitating the one or more antibody-PPT complexes; (iv) amplifying prey nucleic acid sequences associated with the one or more immunoprecipitated antibody-PPT complexes to obtain a plurality of cDNAs comprising nucleic acid sequences corresponding to the amplified prey nucleic acid sequences; and (v) sequencing the plurality of cDNAs to obtain an antigen immunoprofile of the biological sample.

The biological sample to be immunoprofiled can be any biological sample that contains antibodies, including, but not limited to, serum, whole blood, breast milk, saliva, and tears. In some embodiments, a biological sample to be immunoprofiled contains antibodies from multiple subjects suffering from the same health condition or diagnosed as being at risk for the same health condition. This is useful, for example, when differences are sought between control subjects and subjects affected by a particular health condition or predisposition to the health condition, as these "averaged" samples are less prone to random differences in immune response among various individuals, whereas systematic immune-response differences associated with a disease state will tend to be common to patients and will be reflected accordingly in the pooled samples.

In some embodiments, the PPT population contains diverse PPTs containing amino acid sequences from one or more pathogens, as mentioned herein. In some embodiments, the immunoprofiling method is applied to a biological sample (e.g., serum) from a subject exposed to a pathogen, or suspected of having been exposed to a pathogen for which PPT sequences are represented in the PPT library, which would thereby allow a determination/diagnosis of an infection status, or of a prognosis status, e.g., based on the level of antibodies to particular set of pathogen antigens.

In some embodiments, the linked prey RNAs used in the method contain one or more modified ribonucleotides, e.g., biotinylated ribonucleotides or ribonucleotides that are resistant to ribonuclease.

In other embodiments, the PPT population used in the immunoprofiling method contains one or more cancer cell PPTs.

In some embodiments, the step of amplifying the prey RNA sequences comprises incorporating a bar code tag sequence into the plurality of cDNAs resulting from the amplification. For example, where amplification of prey RNAs is performed by PCR, the forward or reverse primer may include a bar code tag sequence that is associated with a particular sample source (e.g., a patient sample). This "bar coding" allows combination of cDNAs amplified from multiple sources/patients to be combined into one sequencing read since each sequence read can be assigned to a particular sample source.

Also provided herein is a method for identifying a disease-associated antigen, that includes the steps of: (i) providing a first biological sample, comprising a plurality of antibodies from one or more control subjects; (ii) contacting the first biological sample with a population of PPTs, wherein each PPT in the population of PPTs is chemically linked to a prey nucleic acid, and wherein the contacting conditions permit binding of one or more of the PPTs with one or more of the antibodies in the plurality of antibodies from the one or more control subjects to obtain one or more control subject antibody-PPT complexes; (iii) immunoprecipitating the one or more control antibody-PPT complexes to obtain a counter-selected PPT population comprising a population of PPTs depleted of PPTS recognized by antibodies present in the first biological sample; (iv) contacting the counter-selected PPT population with a second biological sample comprising a plurality of antibodies from one or more patients suffering from the same health condition or diagnosed as being at risk of suffering from the same health condition to obtain one or more patient antibody-PPT complexes; (v) immunoprecipitating the one or more patient antibody-PPT complexes; (vi) amplifying prey nucleic acid sequences associated with the one or more immunoprecipitated patient antibody-PPT complexes to obtain a plurality of disease antigen-associated cDNAs comprising nucleic acid sequences corresponding to the amplified prey nucleic acid sequences; and (vii) sequencing the plurality of cDNAs to identify the disease-associated antigen. Such a method is a powerful approach to "subtractively" identifying antigens associated with an immune response in a particular health condition. While not wishing to be bound by theory, the rationale is that immunoreactivity to a large set of potential antigens, present in a PPT population, will be common to both control subjects, which are not affected by a particular health condition, and subjects affected by a health condition for which an associated antigen is sought. Thus, by initially reacting a PPT population to control subject antibody-containing samples and immunoprecipitating antibody-bound PPTs, the resulting, unreacted PPT population will be depleted of antigens common to both control and patient samples, and, conversely, will be enriched for one or more health condition/disease-associated antigens.

In some embodiments the prey nucleic acid is a prey RNA encoding the amino acid sequence of the chemically linked PPT. In other embodiments, the prey nucleic acid is a DNA bar code.

In some embodiments, the health condition for which an associated antigen is sought is an autoimmune condition. In other embodiments, the health condition is a pathogen-associated disease or an infectious disease.

In some embodiments, the PPT population used in the method includes antigens associated with an autoimmune condition. In other embodiments, the PPT population includes one or more pathogen PPTs.

Prey RNAs and their associated sequences, as used in the methods and compositions described herein, can be amplified by a number of well known methods in the art, including, but not limited to, RT-PCR, RT followed by RNA amplification with an RNA polymerase (e.g., SP6 or T7 RNA polymerase), and ligase chain reaction.

Complex prey RNA-derived amplicon populations obtained by any of the foregoing exemplary amplification methods can be sequenced in parallel by any of a number of commonly used and well established methods in the art such as "sequencing by synthesis." Platforms for massively parallel sequencing suited for the methods described herein are commercially available from several providers including, but not limited to, Illumina, Pacific Biosciences, LifeTechnologies (Ion Torrent), and Complete Genomics.

The invention will be more fully understood upon consideration of the following non-limiting Examples.

EXAMPLES

Example 1 Multiplexed Detection of Antigens Recognized by a Patient Serum Sample Library Vector Design Using the library collection at DNASU of nearly 12,000 human genes with verified full-length sequences, open reading frames (ORFs) are cloned into expression vectors that include the promoter site for T7 polymerase positioned to drive sense strand transcription of the genes. Optionally, affinity tags are included (e.g., FLAG, HA) in the same reading frame to enable the selection of the mRNA-protein fusions. These clones will be created in Gateway system backbone so that genes can be readily transferred into the vector system in frame and accurately.

Generation of mRNA by In Vitro Transcription

Each mRNA transcript for corresponding genes is transcribed independently in a well plate platform. The transcription reactions is performed as previously described 1. Briefly, each plasmid is incubated with rNTP, $MgCl_2$, T7 polymerase and a suitable buffer at 37° C. for a period of 6-12 hours. After incubation, EDTA is added at room temperature to dissolve the magnesium pyrophosphates. The corresponding reaction mixture is then extracted by phenol/chloroform and the mRNA is desalted. The concentration of all the different mRNA transcripts synthesized will be measured. The mRNA samples are frozen at −20° C. until further use.

Conjugation of mRNA with Puromycin-Oligo Linker

A DNA oligonucleotide 3' terminated in puromycin is conjugated to equimolar concentrations of mRNA molecules synthesized and purified as explained above. The RNA and puromycin linker are annealed on a thermo cycler and then UV irradiated to assist cross-linking between the linker and the mRNA molecules. The puromycin linked mRNA molecule can be precipitated with LiCl and is used for in vitro translation and hybrid formation.

In Vitro Translation and mRNA Protein Hybrid Formation

Puromycin linked mRNA templates are mixed with components for the in vitro translation reaction according to manufacturer's instructions. The translated mixture is treated with appropriate concentrations of $MgCl_2$ and KCl and incubated overnight at −20° C. for fusion formation. Any non-conjugated proteins in the reaction are eliminated by purification with an oligo (dT) column.

Serum Screening

For detecting antibodies in a patient serum sample, different concentrations of serum dilutions are incubated with a pool of mRNA-protein fusion molecules (i.e., PPTs conjugated to "prey" RNAs) to determine the optimum experimental conditions necessary for this reaction. The unbound fraction is separated from the bound fraction by incubating with anti-human IgG magnetic beads. The isolated mRNA-protein hybrids which bind to a serum antibody is then amplified and sequenced using the RNA tag. The identity of the binding candidates is then analyzed by Next Generation Sequencing.

Generation of cDNA from mRNA Protein Fusion

The isolated mRNA-protein hybrids that bind to serum antibodies are first converted into cDNAs. Briefly, the mRNA-protein hybrid sample are incubated with dNTPs, reverse transcription (RT) primer, DTT, first strand RT buffer and RT enzyme at 42° C. for 50 min. After incubation, the RT enzyme is deactivated and the RNA-DNA mixture is incubated with necessary reagents (dNTPs, RNase H, DNA polymerase, DNA ligase, second strand buffer etc) to synthesize the double stranded cDNAs. The cDNAs are then purified using a PCR purification kit and used for library preparation to perform RNA-Seq.

Library Preparation for RNA-Seq

The cDNA samples obtained are first fragmented with DNase 1 to generate small fragments of cDNA. The resultant short fragments are purified and end repaired to convert any overhangs into blunt ends. Further modifications are incorporated to facilitate the ligation of illumina adaptors. Alternatively, the DNA is fragmented using a Covaris sonicator according to the manufacturer's instructions. The adapters (supplied by Illumina) with unique bar coding sequences are subsequently ligated to each end of cDNA fragment. The samples are then purified to remove any excess adapters and PCR amplified to generate a cDNA library to be sequenced using an Illumina platform for Next Generation Sequencing. The sequence reads are then subjected to bioinformatic analysis to identify the antigen candidates that bind to antibodies in the patient serum samples.

REFERENCES

1. Cotton S W et al.; *Nature Protocols.* 2011, (6), 1163-2011
2. Liu R et al.; Methods in Enzymology. 2000, (318), 268-293
3. Shen X et al.; PNAS. 2005, (102), 5969-5974

Example 2 Use of DNA "Bar Code"-Linked Prey Polypeptide Targets

Figure 4:
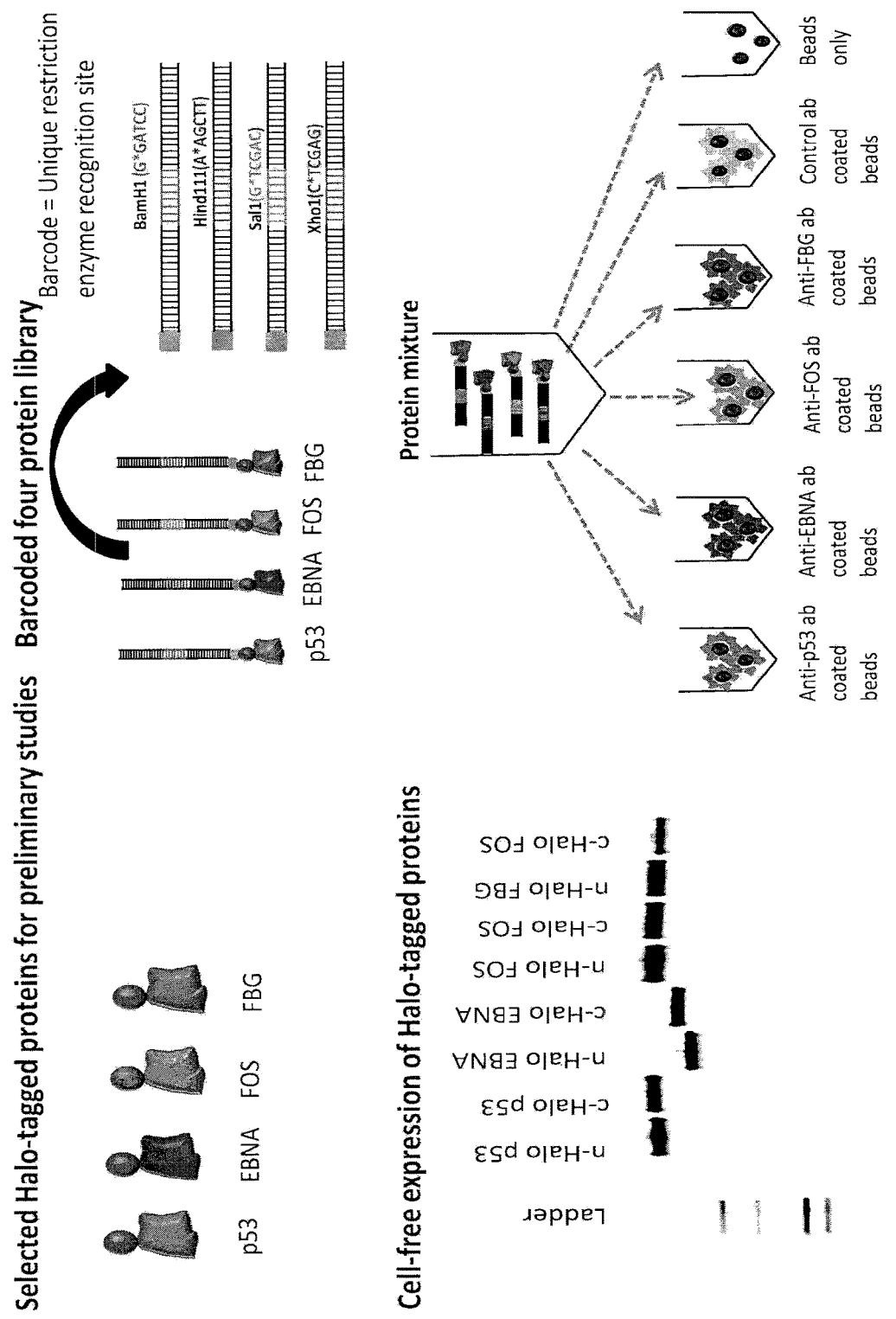
FIG. 4 Schematic illustration of nucleic acid bar codes containing different restriction enzyme sites. Each HaloTag® ligand-conjugated DNA bar code contains a distinct restriction site. Separate tagging of p53, EBNA, FOS, and FBG HaloTag® fusion polypeptides with each DNA Bar Code HaloTag® ligand allows subsequent identification of tagged, immunoprecipitated proteins by restriction digest of the DNA bar codes with restriction enzyme that cleaves the unique restriction site.
Figure 5:
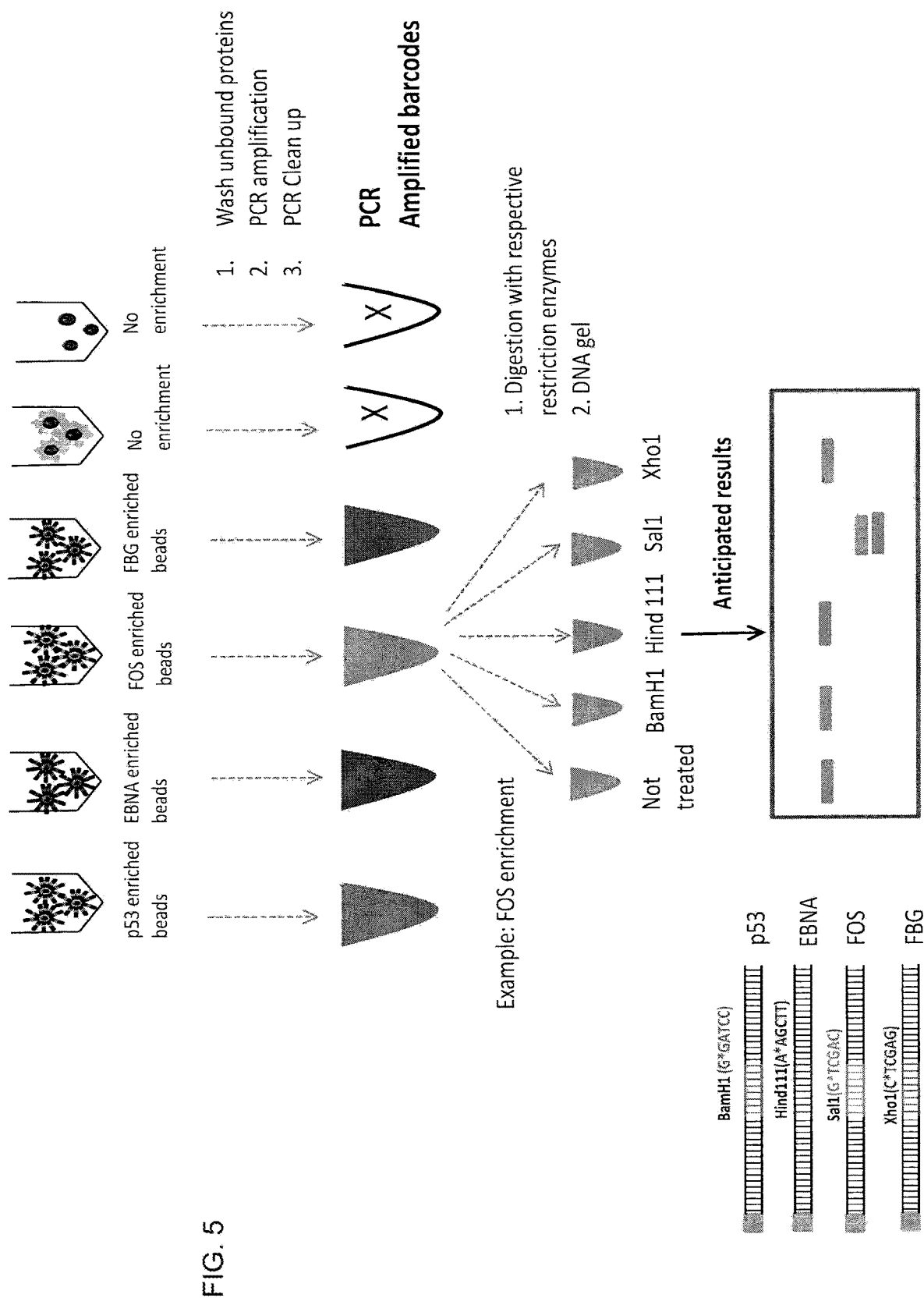
FIG. 5 Schematic overview of a restriction enzyme based assay for bar codes attached to proteins. Four proteins (each bar-coded by a different nucleic acid with a known restriction site) are mixed together. In this example, an antibody to FOS is added and used to separate out all FOS protein. The bar code on the captured protein is amplified and digested with enzymes that correspond to each of the bar codes for the four proteins. Only the enzyme that recognizes the bar code attached to fos leads to cleavage of the barcode sequence.

Materials and Methods
Generation of Halotagged Fusion Proteins n-Halo and c-Halo tagged p53, EBNA, FOS and FBG were expressed in human coupled in vitro protein expression system (Thermo scientific). Protein expression was analyzed by incubating the proteins with 4 µM of Halo tag fluorescent ligand (Promega) followed by 4-20% SDS-PAGE gel analysis (FIG. 4). Full length expression was observed for all proteins except for n-Halo tagged EBNA.
Barcode, Halo-Ligand Hybridization Equimolar concentration of DNA conjugated Halo-ligand was mixed with four different DNA barcodes in separate wells in the presence of buffer (10 mM Tris-HCl, 50 mM NaCl, 10 mM $MgCl_2$, 1 mM DTT, pH 7.8) and 25 mM dNTP. The mixture was heated to 95° C. for two minutes and cooled gradually to room temperature for one hour, followed by klenow extension with 0.5 unit of Exo⁻Klenow polymerase (New England Biolabs) for 30 min at 37° C. The hybridized Halo ligand-DNA barcodes were stored at −20° C. until use.
Generation of a DNA Bar Coded Four Protein Library Four unique Halo ligand-DNA barcodes (10 ng/µL) were added to c-Halo tagged p53, EBNA, FOS and FBG proteins. The samples were incubated on ice for 1 hour for covalent bond formation. Then, Halo ligand (4 mM) without a DNA barcode was added and incubated for 1 hour on ice to block any unbound sites. Equal concentration of barcoded p53, EBNA, FOS and FBG were mixed together to make the four protein library. The protein mixture was kept on ice.
Pull-Down Assays Magnetic Dynabeads protein G (Life technologies) particles were washed with ice cold PBST (PBS with 0.2% Tween-20) three times and incubated with 1:1000 diluted (PBST) anti-p53, anti-EBNA, anti-FOS and anti-FBG antibodies in separate wells at RT for 2 hours. Then, the beads were washed with ice-cold PBST five times and incubated with the four protein library at room temperature for two hours with shaking. The supernatant was removed and washed with ice-cold PBST six times and 100 µL of PBS was added to the beads after the final wash. The beads were stored at −20° C.

For serum autoantibody studies 1:500 diluted EBNA positive sera and EBNA negative sera was incubated with protein A/G magnetic beads (Life technologies) at room temperature for two hours. The serum coated beads were washed with ice-cold PBST five times and incubated with the four protein library at room temperature for two hours. The beads coated with EBNA positive and negative sera without incubation with the four protein library were used as the control. The beads were then washed six times with ice cold PBST and resuspended in 100 µL of PBS.
PCR, qPCR and Restriction Enzyme Digestion The beads from the pull down assays were subjected to PCR with universal forward and reverse primers. The following thermal cycles were used for PCR: 98° C., 30 sec, 98° C., 10 sec; 58° C., 30 sec and 72° C., 1 sec; 20 cycles. After PCR, the supernatant was separated from the magnetic beads and the bands were resolved on a 1% agarose gel. qPCR was performed with Platinum SYBR Green qPCR-system (Applied Biosystems) on a QuantStudio Dx Real Time Instrument (Applied Biosystems). The fold change was normalized to control ab.

To identify the enriched antigens the PCR products were treated with respective restriction enzymes BamH1, Hind111, and Sal1 at 37° C. for three hours. The samples were analyzed on a 3% TBE gel along with un-digested PCR products.

Figure 6:
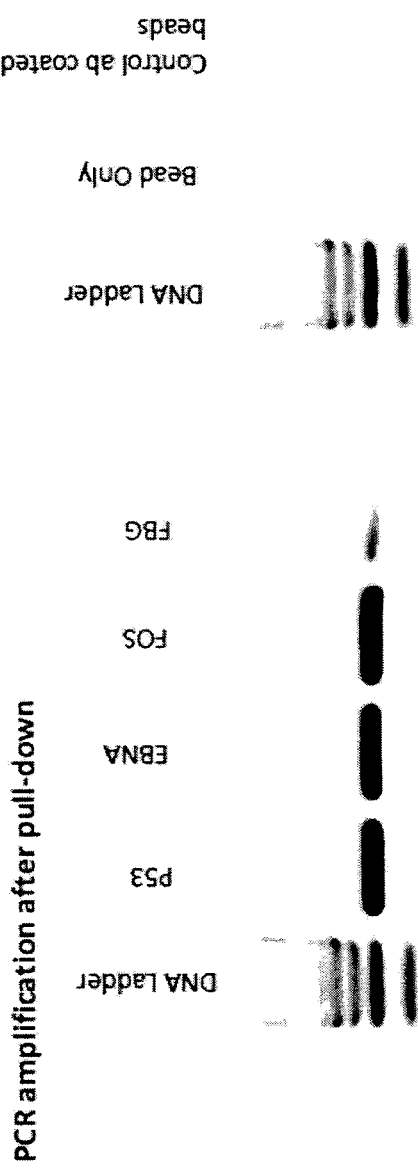
FIG. 6 Proteins tagged with nucleic acids are efficiently captured by antibodies targeting each proteins. The antibody targeting FBG was less efficient than the other antibodies. qPCR data show that amplification of the relevant bar-code yielded DNA amounts that correlate with the level of protein captured.
Figure 6:
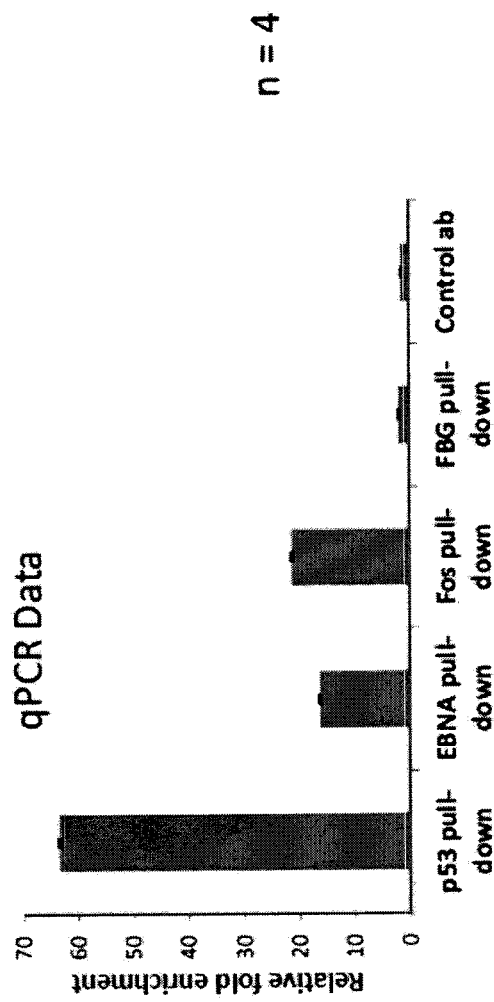
Figure 7:
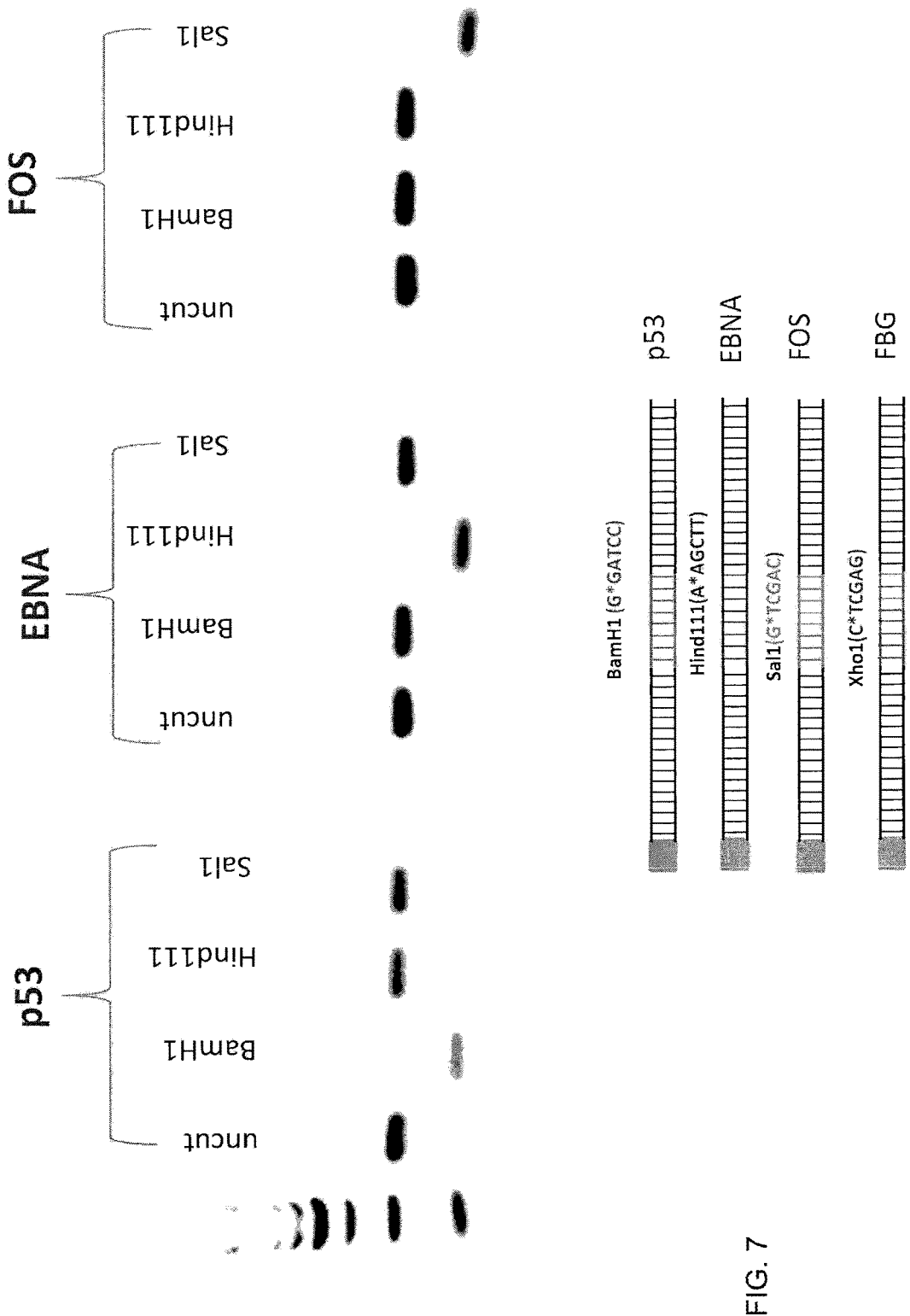
FIG. 7 Demonstration of the restriction enzyme based detection of bar code labeled proteins. Antibodies to p53, EBNA and FOS were used to immunoprecipitate each of these proteins, respectively. The nucleic acids attached to the captured proteins were amplified and subjected enzymes corresponding to each of the attached bar codes, respectively. Only the enzyme that corresponded to the barcode attached to the relevant protein cleaved the amplified DNA. For example, in p53 immunoprecipitations, only BamHI cleaved the amplified DNA.
Figure 8:
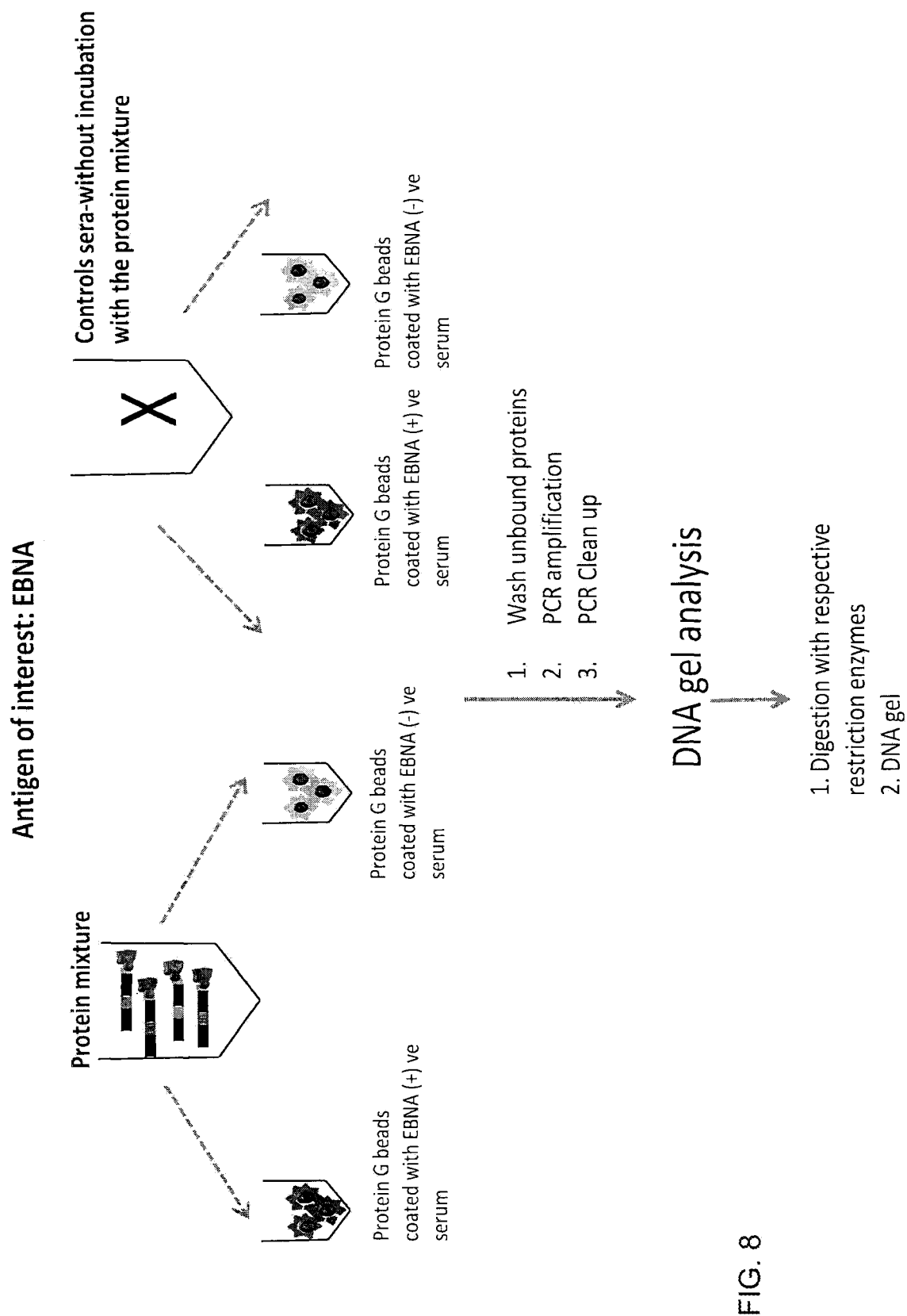
FIG. 8 Schematic overview of experiment to test serum with nucleic acid tagged proteins to identify serum autoantibodies. A mixture of HaloTag® fusion polypeptides ("protein mixture") is added to protein G beads coated with serum from a subject exposed to Epstein-Barr virus (comprising the Epstein-Barr Nuclear Antigen-1 protein) "EBNA (+) ve" serum or serum from a subject not previously exposed to Epstein-Barr virus ("EBNA (−) ve" serum. EBNA antibodies present in EBNA (+) ve serum will bind to and be immunoprecipitated with EBNA-DNA-Bar coded HaloTag® fusion polypeptides, whereas few or no EBNA antibodies are found in the EBNA (−) ve serum, and therefore no immunoprecipitation (or much less) of the EBNA-DNA-Bar coded HaloTag® fusion polypeptide will occur in this sample.

The PCR amplification of p53, EBNA, and FOS pull-down assays show amplified PCR products with ~100 bp, in agreement with expected size (FIG. 6). FBG enrichment did not produce an amplified band under the current experimental conditions. It was noted that the FBG antibody was weak compared to the other antibodies used in the assay, and a higher concentration would be needed for effective response. The amplification from the control antibody coated beads and the bead only control was negligible. The qPCR data further substantiates the above observation by showing that p53, EBNA and FOS were enriched by their antibodies, but not by the control antibody. The amplified PCR products for p53, EBNA and FOS only get digested with the restriction enzymes consistent with the unique DNA barcode sequence (FIG. 7). This demonstrated the specificity of this technique.

Figure 9:
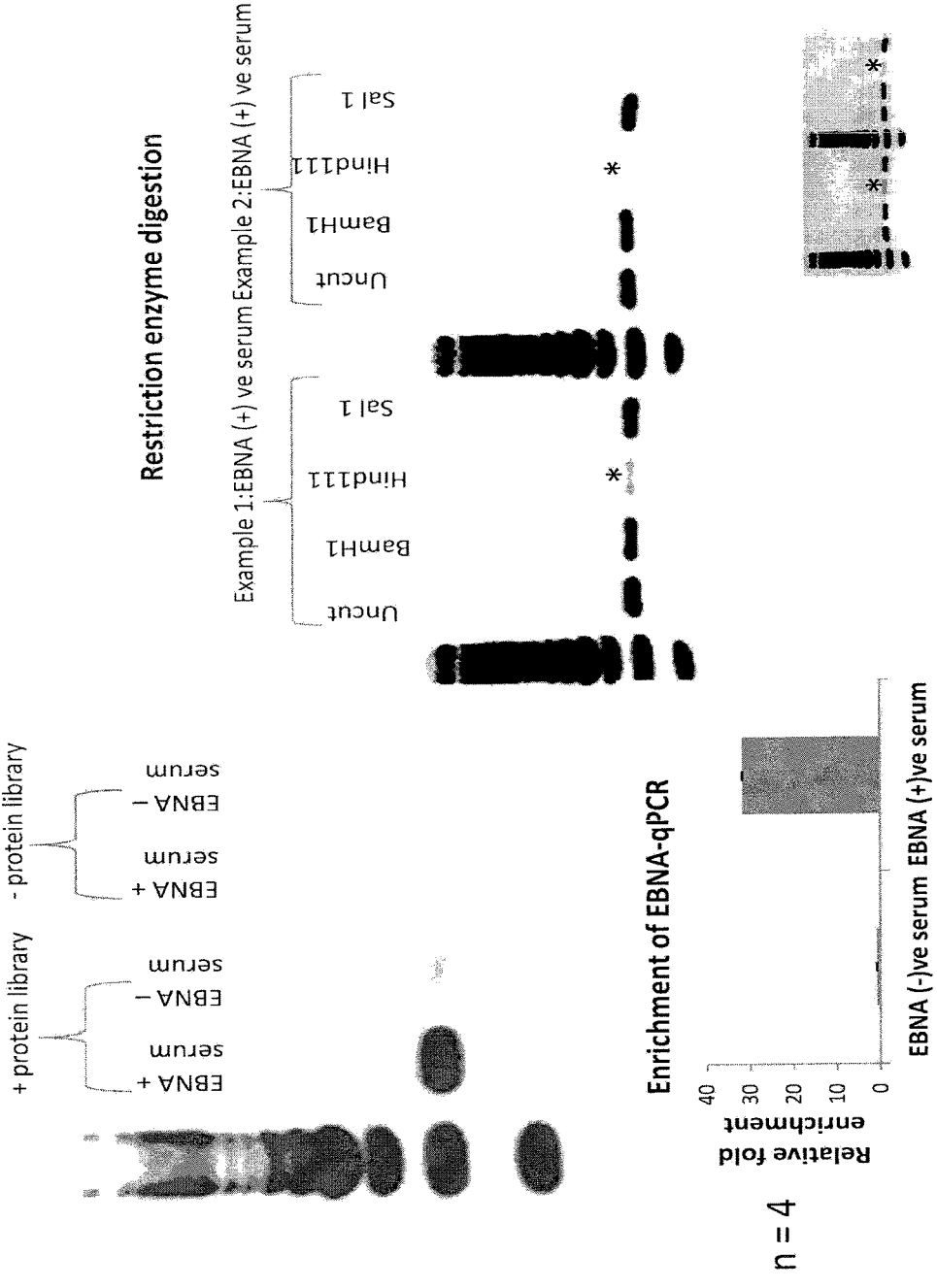
FIG. 9 Demonstration of detection of serum response against EBNA protein using nucleic acid tagged proteins. EBNA responsive serum and EBNA non-responsive serum were used to immunoprecipitate a mixture of nucleic acid tagged proteins. The nucleic acid tags were amplified and tested with various restriction enzymes. DNA amplified from the EBNA responsive serum was specifically digested by HindIII, which was the bar code attached to the EBNA protein. qPCR revealed that only the EBNA responsive serum (and not the EBNA non-responsive serum) amplified the appropriate nucleic acid barcode.

The results shown in FIG. 9 demonstrated the enrichment of the EBNA antigen in an individual with serum antibodies against EBNA. Both PCR and qPCR data indicates enrichment in the EBNA positive serum, but not the EBNA negative serum or the serum in the absence of the four protein library.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A multiplexed polypeptide affinity assay (MPA) composition comprising a population of prey polypeptide targets (PPTs), wherein
   each PPT in the population is chemically linked to a prey nucleic acid, wherein the prey nucleic acid is an RNA encoding the amino acid sequence of the chemically linked PPT,
   a largest difference between a first PPT representation in the population and a second PPT representation in the population is no greater than ten-fold; and
   the PPT population comprises fusion polypeptides comprising the amino acid sequence of a haloalkane dehalogenase tag polypeptide fused at the N-terminus or C-terminus of the fusion polypeptides, and wherein the prey nucleic acid is chemically linked to a ligand that reacts specifically with and becomes covalently linked to the haloalkane dehalogenase tag polypeptide.

2. The MPA composition of claim 1, wherein the RNA comprises one or more modified ribonucleotides.

3. The MPA composition of claim 1, wherein the prey nucleic acid comprises a DNA bar code.

4. The MPA composition of claim 1, wherein the PPT population comprises fusion polypeptides comprising the amino acid sequence of a haloalkane dehalogenase tag polypeptide fused at the N-terminus or C-terminus of the fusion polypeptides, and wherein the prey nucleic acid is chemically linked to a ligand that reacts specifically with and becomes covalently linked to the haloalkane dehalogenase tag polypeptide.

5. The MPA composition of claim 1, wherein the PPT population comprises a plurality of amino acid sequences from a plurality of pathogens.

6. The MPA composition of claim 5, wherein the plurality of amino acid sequences comprises amino acid sequences of viral pathogens, bacterial pathogens, eukaryotic pathogens, or a combination thereof.

7. The MPA composition of claim 1, wherein the PPT population comprises a plurality of amino acid sequences from a plurality of antigens associated with one or more autoimmune diseases.

8. The MPA composition of claim 1, wherein the PPT population comprises a plurality of polypeptides comprising random amino acid sequences.

9. The MPA composition of claim 1, further comprising a population of bait polypeptides comprising diverse amino acid sequences, wherein at least one of the bait polypeptides binds to at least one of the PPTs.

10. The MPA composition of claim 9, wherein the population of bait polypeptides comprises a plurality of antibodies with diverse antigen specificities.

11. The MPA composition of claim 10, wherein the population of bait polypeptides comprises serum.

12. The MPA composition of claim 10, further comprising a polypeptide that binds specifically to the Fc region of an immunoglobulin.

13. The MPA composition of claim 12, wherein the polypeptide that binds specifically to the Fc region of an immunoglobulin is Protein G, Protein A, Protein A/G, or an antibody that binds specifically to the Fc region of an immunoglobulin.

14. The MPA composition of claim 10, wherein the plurality of antibodies are biotinylated antibodies.

15. The MPA composition of claim 9, wherein the population of bait polypeptides comprises diverse amino acid sequences from at least one of transcription factors, G-proteins, receptors, protein kinases, protein phosphatases, proteases, or a combination thereof.

16. The MPA composition of claim 15, wherein the population of bait polypeptides consists essentially of a population of diverse amino acid sequences from one or more of G-proteins, receptors, protein kinases, protein phosphatases, proteases, or a combination thereof.

17. A kit, comprising:
   (i) a PPT library, wherein each PPT in the library is chemically linked to a prey nucleic acid, and wherein the relative abundance of PPTs in the population falls within about a ten fold range, wherein the PPT library comprises fusion polypeptides comprising the amino acid sequence of a haloalkane dehalogenase tag polypeptide fused at the N-terminus or C-terminus of the fusion polypeptides, and wherein the prey nucleic acid is chemically linked to a ligand that reacts specifically with and becomes covalently linked to the haloalkane dehalogenase tag polypeptide; and
   (ii) forward and reverse oligonucleotide primers to amplify the prey nucleic acid.

18. The kit of claim 17, wherein the prey nucleic acid comprises a DNA bar code.

19. The kit of claim 17, wherein the PPT library comprises a plurality of amino acid sequences from a plurality of pathogens.

20. The kit of claim 17, wherein the PPT library comprises a plurality of amino acid sequences from a plurality of antigens associated with autoimmune diseases.

* * * * *